United States Patent
Kim et al.

(10) Patent No.: US 10,172,768 B2
(45) Date of Patent: Jan. 8, 2019

(54) COSMETIC COMPOSITION CONTAINING JADE POWDER FOR BLOCKING BLUE LIGHT

(71) Applicant: AMOREPACIFIC CORPORATION, Seoul (KR)

(72) Inventors: Hyoung June Kim, Yongin-si (KR); Ji Young Lee, Yongin-si (KR); Hyun Suk Lee, Yongin-si (KR); Yu Chul Jung, Yongin-si (KR); Ga Young Cho, Yongin-si (KR); Dong Wook Shin, Yongin-si (KR); Tae Ryong Lee, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 15/576,173

(22) PCT Filed: Jun. 13, 2016

(86) PCT No.: PCT/KR2016/006262
§ 371 (c)(1),
(2) Date: Nov. 21, 2017

(87) PCT Pub. No.: WO2017/003111
PCT Pub. Date: Jan. 5, 2017

(65) Prior Publication Data
US 2018/0133125 A1 May 17, 2018

(30) Foreign Application Priority Data

Jun. 30, 2015 (KR) .......................... 10-2015-0092999
Jun. 13, 2016 (KR) .......................... 10-2016-0072931

(51) Int. Cl.
| A61K 8/19 | (2006.01) |
| A61K 8/02 | (2006.01) |
| A61Q 17/04 | (2006.01) |

(52) U.S. Cl.
CPC ................ *A61K 8/19* (2013.01); *A61K 8/022* (2013.01); *A61K 8/0241* (2013.01); *A61Q 17/04* (2013.01)

(58) Field of Classification Search
CPC combination set(s) only.
See application file for complete search history.

(56) References Cited

U.S. PATENT DOCUMENTS 4,857,306 A * 8/1989 Roller ..................... A61K 8/19
106/401
2003/0031869 A1 2/2003 Vagarali et al.
(Continued)

FOREIGN PATENT DOCUMENTS

JP 2001226247 A 8/2001
JP 2006306827 A 11/2006
(Continued)

OTHER PUBLICATIONS

KR application 20070011404 published Jan. 4, 2008 as KR100791212B1 (English translation) 12 pages. (Year: 2008).*
(Continued)

*Primary Examiner* — Ernst V Arnold
(74) *Attorney, Agent, or Firm* — Lucas & Mercanti, LLP

(57) ABSTRACT

The present invention relates to a cosmetic composition which contains jade powder so as to block blue light in the visible spectrum. The composition, containing jade powder as an active ingredient, for blocking blue light is capable of specifically reflecting and thus blocking light in the blue light spectrum, which has been difficult to block, thereby protecting the skin.

4 Claims, 4 Drawing Sheets

(56) References Cited

U.S. PATENT DOCUMENTS

| | | | | |
|---|---|---|---|---|
| 2006/0134155 | A1* | 6/2006 | Dryer | A61K 8/442 424/401 |
| 2011/0262560 | A1* | 10/2011 | Dabe | A61K 8/19 424/646 |

FOREIGN PATENT DOCUMENTS

| | | | |
|---|---|---|---|
| JP | 2007308395 | A | 11/2007 |
| JP | 2008050242 | A | 3/2008 |
| JP | 2011020948 | A | 2/2011 |
| JP | 5283111 | B2 | 9/2013 |
| KR | 19990078684 | A | 11/1999 |
| KR | 100279694 | B1 | 1/2001 |
| KR | 20010077370 | A | 8/2001 |
| KR | 20010105111 | A | 11/2001 |
| KR | 20030052714 | A | 6/2003 |
| KR | 20050118258 | A | 12/2005 |
| KR | 20080017195 | A | 2/2008 |

OTHER PUBLICATIONS

Hydroxyethyl acrylate/sodium acryloyldimethyl taurate copolymer [online] retrieved on Sep. 7, 2018 from: https://www.ewg.org/skindeep/ingredient/703053/HYDROXYETHYL_ACRYLATE%3B%3B_SODIUM_ACRYLOYLDIMETHYL_TAURATE_COPOLYMER/#.W5JouDbruF4; 2 pages. (Year: 2018).*

Godley et al., "Blue Light Induces Mitochondrial DNA Damage and Free Radical Production in Epithelial Cells*", The Journal of Biological Chemistry, 2005, vol. 280, No. 22, Issue of Jun. 3, pp. 21061-21066.

Liebmann et al., "Blue-Light Irradiation Regulates Proliferation and Differentiation in Human Skin Cells", Journal of Investigative Dermatology, 2010, vol. 130, pp. 259-269.

Kim et al., "Violet Light Down-Regulates the Expression of Specific Differentiation Markers through Rhodopsin in Normal Human Epidermal Keratinocytes", PLOS ONE, 2013, vol. 8, Issue 9, e73678, pp. 1-10.

International Search Report for International Application No. PCT/KR2016/006262 (2 Pages) (dated Sep. 30, 2016).

* cited by examiner

COSMETIC COMPOSITION CONTAINING JADE POWDER FOR BLOCKING BLUE LIGHT

CROSS-REFERENCE TO RELATED APPLICATIONS

This application is a 371 of PCT/KR2016/006262, filed on Jun. 13, 2016 which claims the benefit of Korean Patent Application No. 10-2015-0092999, filed Jun. 30, 2015 and Korean Patent Application No. 10-2016-0072931, filed Jun. 13, 2016 the contents of each of which are incorporated herein by reference.

TECHNICAL FIELD

The present invention relates to a cosmetic composition containing jade powder for blocking blue light in the visible spectrum.

BACKGROUND ART

In general, what people call 'light' refers to visible light in the light spectrum (380 to 780 nm) which can be seen with human eyes among various electromagnetic waves. Among these, blue light refers to visible light which people can see as light having a wavelength of 380 to 500 nm, that is, light having the shortest wavelengths and the strongest energy in light that reaches the retina. In particular, light having a wavelength range of 380 to 430 nm is classified as violet light in the blue light spectrum.

Little is known about effects of light with the other wavelengths (e.g., visible light) other than ultraviolet rays on the human skin, but adverse effects of blue light on the skin have been recently investigated.

As published in this regard, the article (THE JOURNAL OF BIOLOGICAL CHEMISTRY Vol. 280, No. 22, Issue of June 3, pp. 21061-21066, 2005 "Blue Light Induces Mitochondrial DNA Damage and Free Radical Production in Epithelial Cell") reports that blue light causes damages to mitochondrial DNA of epithelial cells and generates reactive oxygen species (ROS) therein to cause cellular dysfunction, cellular aging, and oncogenesis.

Also, another article (Journal of Investigative Dermatology (2010) 130, 259 to 269 "Blue-Light Irradiation Regulates Proliferation and Differentiation in Human Skin Cells") reports that light having a wavelength of 412 to 453 nm regulates the growth and differentiation of keratinocytes and skin-derived endothelial cells, and still another article (PLoS One. 2013 Sep. 17; 8(9)e73678 "Violet Light Down-Regulates the Expression of Specific Differentiation Markers through Rhodopsin in Normal Human Epidermal Keratinocytes") reports that violet light (410 nm) in the blue light spectrum overexpresses mRNA of rhodopsin among photoreceptors expressed in keratinocytes of the skin to reduce the phosphorylation of cAMP responsive element-binding proteins (CREBs) and reduce mRNA expression levels of keratin-10 (K10) and keratin-1 (K1) as differentiation markers for certain horny cells, resulting in reduced differentiation of human keratinocytes and delayed recovery of damaged skin barriers.

In addition to the known effects on the skin, blue light causes sleep disorders by suppressing a secretion rate of melatonin, which induces a sleeping state, and increasing a secretion rate of serotonin, which induces a waking state, and also makes the skin look dull and gives freckles by inducing melanogenesis when it directly reaches the retinae.

Because a lot of blue light is emitted from the necessities of modern people, especially from LED displays and LED lightings such as smartphones, laptop computers, monitors, etc., the people cannot help coming in unavoidable contact with the blue light under living environments in the modern society. Therefore, there have been attempts conducted to block the blue light in many ways. Among these various attempts, however, there is neither disclosure nor teaching regarding the jade powder's effect of blocking blue light. Accordingly, the present inventors have conducted research for a long period of time, and found that jade powder has an effect of blocking blue light. Therefore, the present invention has been completed based on these facts.

PRIOR-ART DOCUMENT

Korean Registered Patent No. 10-0279694 "Cosmetics Which Contains Nephrite Jade Powder and Process for Preparing Thereof"

DISCLOSURE

Technical Problem

Although it has been recently reported that blue light having a wavelength of 380 to 500 nm in the visible spectrum has lots of problems in that it develops skin barrier dysfunction due to the mitochondrial DNA damage in skin epithelial cells and the inhibited differentiation of keratinocytes, there is no realistic way to protect the skin from blue light because blue light is not effectively blocked even by sunscreen agents.

Technical Solution

Therefore, the present invention is designed to solve the problems of the prior art, and it is an object of the present invention to provide a cosmetic composition for blocking blue light, which contains jade powder as an active ingredient. The jade powder of the present invention may be Chuncheon jade powder, and the size of the jade powder may be in a range of 10 nm to 100 μm. As the composition containing jade powder based on the total weight of the cosmetics, the cosmetic composition may be formulated into any one form selected from toners, lotions, creams, sera, emulsions, nourishing serums, powders, foundations, sprays, mask packs, sheet packs, sleeping packs, wash-off packs, and peel-off packs.

Advantageous Effects

When the cosmetic composition for blocking blue light, which contains jade powder as an active ingredient, is applied, the cosmetic composition can be useful in specifically reflecting light in the blue light spectrum, which has been difficult to block to blocking the light, thereby protecting the skin therefrom.

BEST MODE

Figure 1:
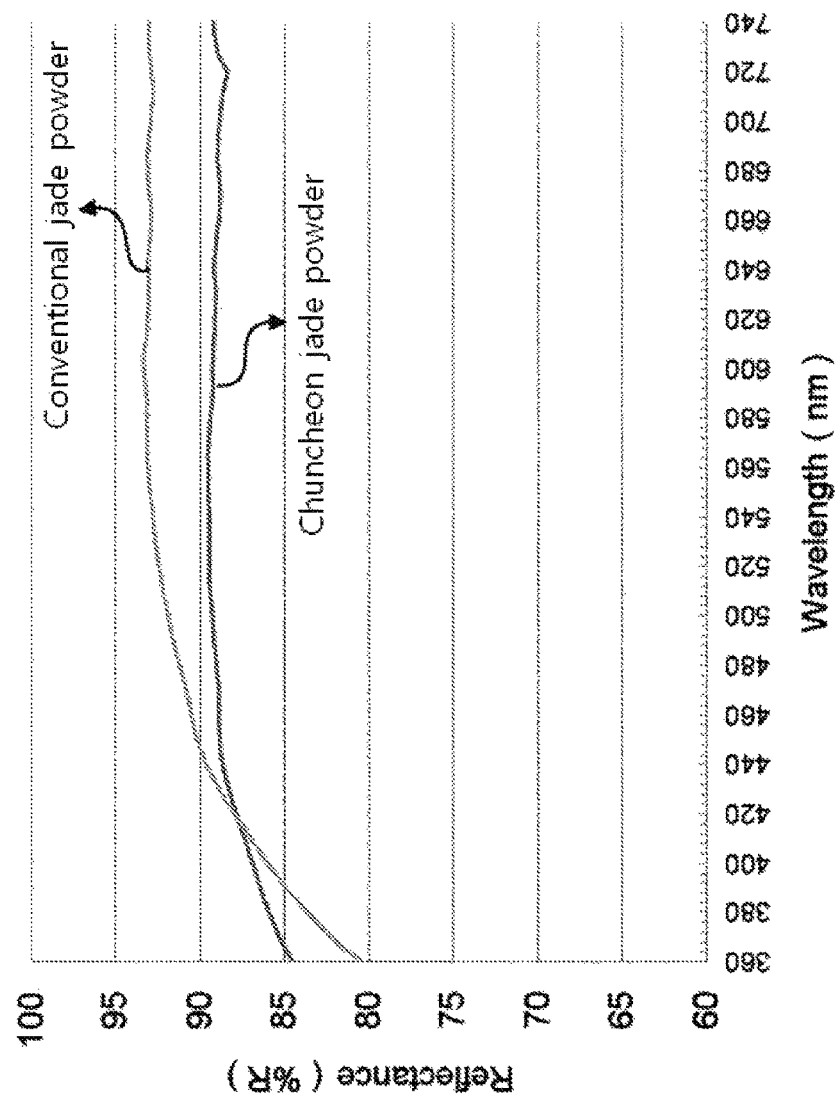
FIG. 1 shows the reflectance spectra of conventional jade powder and Chuncheon jade powder in a wavelength range of 360 to 740 nm.

The present invention discloses a cosmetic composition for blocking blue light, which contains jade powder as an active ingredient. Hereinafter the present invention will be described in further detail with reference to specific embodiments thereof. Unless otherwise defined in this specification, all the technical and scientific terms used herein have the same meanings as what are generally understood by a person skilled in the related art to which the present invention belongs. Therefore, repeated descriptions of the same technical configurations and actions as in the prior art are omitted for clarity.

According to the present invention, jade powder having an ability to block blue light is included in the cosmetics to prevent an adverse effect on the skin among various kinds of harmfulness of blue light known in the art.

In general, jade is divided into jadeite jade and nephrite jade. Jadeite jade generally referred to as "jade" is a monoclinic mineral belonging to the pyroxene family, and has a chemical composition including silicic acid ($[SiO_x(OH)_{4-2x}]_n$), aluminum oxide ($Al_2O_3$) and sodium carbonate ($Na_2CO_3$). The jadeite jade is transparent or translucent with black, bluish green or green color, and has a hardness of 7 in the form of a dense lump such as rock crystal. In this case, the term "jade" generally refers to jadeite jade.

Meanwhile, nephrite jade is a monoclinic mineral of inosilicates belonging to the amphibole family, and a main mineral of nephrite jade is tremolite having a chemical formula: $Ca_2Mg_5(Si_4O_{11})_2(OH)_2$. In this case, when the jade should contain more than 95% tremolite and amphibole, the jade is approved as nephrite jade. A chemical composition of the nephrite jade generally consists of calcium oxide (CaO), magnesium oxide (MgO), and silicon dioxide ($SiO_2$), and pure tremolite does not contain iron oxide (FeO). In effect, however, the mineral of nephrite jade may often contain up to 3% iron oxide (FeO) because magnesium (Mg) is converted into iron (Fe).

According to a German medical literature [Mauda Palmer Die Verborgene of "KRAFF der KRISTALLE and der EDELSTEINE"] published about such jade, as the two different ores, both jadeite and nephrite jade include silicon and oxygen, like most of other jewels. However, jadeite jade is formed of granular crystals while nephrite jade consists of lots of crystals and aggregates of microparticles having a fibrous texture. In particular, nephrite jade includes three minerals, that is, calcium (Ca), iron (Fe) and magnesium (Mg), all of which are good for the human body, as main components unlike jadeite jade including sodium and aluminum components, is not harmful to the human body, and has nontoxicity and non-pungency characteristics.

Also, Chuncheon jade used in the present invention is a kind of nephrite jade, that is, high-quality nephrite jade produced in the Chuncheon area of Gangwon-do. In this case, Chuncheon jade is a mineral having a compact and delicate texture as altered minerals of tremolite and actinolite of the amphibole family, and has a pilotoxitic texture with strong toughness.

In the present invention, the jade having an effect of blocking blue light and directly applicable to the skin as a cosmetic composition is not limited to jadeite jade or nephrite jade. More preferably, the jade is nephrite jade. Also, the color, minor components, a processing method, and the place of origin of the jade are not limited. Also, the jade of the present invention is processed into powder by grinding the jade. In this case, various methods of grinding jade are known in the art, but may be carried out using conventional methods by those skilled in the art. Also, there is no limitation on the methods of grinding jade.

There is the prior art in which the cosmetics contains jade powder, but, in this case, the jade powder is not used in recognition of a blue light-blocking effect, but to have known effects, such as a skin moisturizing effect, activated cell functions, a waste-removing effect, promoted metabolisms, improved blood circulation, etc. On the other hand, the present invention differs from the prior art in that the blue light-blocking effect of jade powder is newly found and the jade powder is then applied to cosmetic compositions.

In the present invention, the jade powder that may be used as a cosmetic composition preferably has a particle size of 10 nm to 100 µm. When the particle size is less than 10 nm, the jade powder has a poor effect of blocking blue light. On the other hand, when the particle size is greater than 100 µm, the jade powder has a rough sense of feeling in use as cosmetics.

Also, the jade powder may be included at a content of 0.05 to 5.0% by weight, more preferably 0.1 to 1.0% by weight, based on the total weight of the cosmetics. When the content of the jade powder becomes higher, the jade powder has a higher blue light-blocking rate. However, when the jade powder is included at an excessive content, the inherent natures or softness of raw materials for cosmetics, and a sense of feeling in use upon application to the skin may be degraded, and an increase in unit price of products may also be caused due to expensive jade. On the other hand, when the jade powder is included at a very small content, it is undesirable because it is impossible to expect the jade powder to have a blue light-blocking effect.

Further, in addition of the jade powder, the cosmetic composition of the present invention may further include functional additives for improvement of skin conditions, such as improvement of skin wrinkles, improvement of skin whitening, improvement of skin elasticity, improvement of facial skin sagging, improvement of skin moisturizing, skin gloss improvement, skin aging prevention (e.g., inhibition of skin wrinkle formation and dermatosclerosis caused by photoaging), improvement of dark circles, and improvement of horny skin; functional additives for blocking ultraviolet rays; or components included in conventional cosmetic compositions.

The functional additives for improvement of skin conditions may include components selected from the group consisting of water-soluble vitamins, fat-soluble vitamins, high-molecular-weight peptides, high-molecular-weight polysaccharides, sphingolipids, natural extracts, and fermented materials. Also, the functional additive for blocking ultraviolet rays may further include inorganic powders such as titanium dioxide ($TiO_2$), zinc oxide (ZnO), etc. In addition, the components included in the conventional cosmetic compositions may be further blended together with the functional additives, when necessary.

Blending components included in addition to the aforementioned components may include oily components, moisturizing agents, emollients, surfactants, organic and inorganic pigments, organic powders, UV absorbing agents, preservatives, disinfectants, antioxidants, plant extracts, pH regulators, alcohols, dyes, fragrances, blood flow stimulants, cooling agents, anhydrotics, purified water, etc., but the present invention is not limited thereto.

The cosmetic composition according to the present invention may be formulated into any one form selected from toners, lotions, creams, sera, emulsions, nourishing serums, powders, foundations, sprays, mask packs, sheet packs, sleeping packs, wash-off packs, and peel-off packs, more preferably may be formulated into mask packs, sheet packs, sleeping packs, wash-off packs, peel-off packs, etc., but is not limited to the formulations.

MODE FOR INVENTION

Hereinafter, the present invention will be described in further detail with reference to specific embodiments thereof. However, it will be apparent to those skilled in the art that the present invention is not limited to the embodiments disclosed below, but various modifications and changes can be made to the aforementioned exemplary embodiments of the present invention. The following embodiments are put into practice to verify a blue light-blocking effect of jade powder.

As the jade powder to be used below, conventional jade powder (commercially available from Jinu Costech Co.) and Chuncheon jade powder (commercially available from Oksanga Co. Ltd.) were prepared. Thereafter, the reflectance spectra of subjects for tests corresponding to the following experiments were measured at a wavelength range of 360 to 740 nm using a color difference meter (ColorMate commercially available from Scinco Co. Ltd., Korea). Then, PC software, ColorMaster, for operation of ColorMate was used to measure the reflectance. The reflectance was measured to determine a blue light-blocking rate in the corresponding spectrum.

Experimental Example 1. Measurement of Reflectance (% R) of Jade Powder

To determine the reflectance (or transmittance) of the conventional jade powder and the Chuncheon jade powder, an experimental method designed by Scinco Co. Ltd. (#627, Bongeunsa-ro, Gangnam-gu, Seoul, Korea) was carried out using a color spectrophotometer (Model: ColorMate).

FIG. 1 shows the reflectance spectra of conventional jade powder and Chuncheon jade powder in a wavelength range of 360 to 740 nm. As seen from the data of FIG. 1, it was revealed that both of the conventional jade powder and the Chuncheon jade powder had high reflectance in the entire visible light spectrum (380 to 740 nm), particularly that the Chuncheon jade powder reflected light with less than approximately 420 nm (the violet light spectrum of the strongest energy in the blue light) and the conventional jade powder reflected light with 420 nm or more, indicating that the Chuncheon jade powder and the conventional jade powder had high light-blocking rates in the entire visible light spectrum.

Experimental Example 2. Measurement of Reflectance (% R) in Artificial Leather To measure the reflectances (light-blocking rates) of the conventional jade powder and the Chuncheon jade powder at specific wavelengths, the powder of each of the conventional jade powder and the Chuncheon jade powder was applied onto artificial leather at a content of 1 mg/cm$^2$, and the spectra on the powder-coated artificial leathers at 360 to 740 nm were analyzed using a spectrophotometer.

Figure 2:
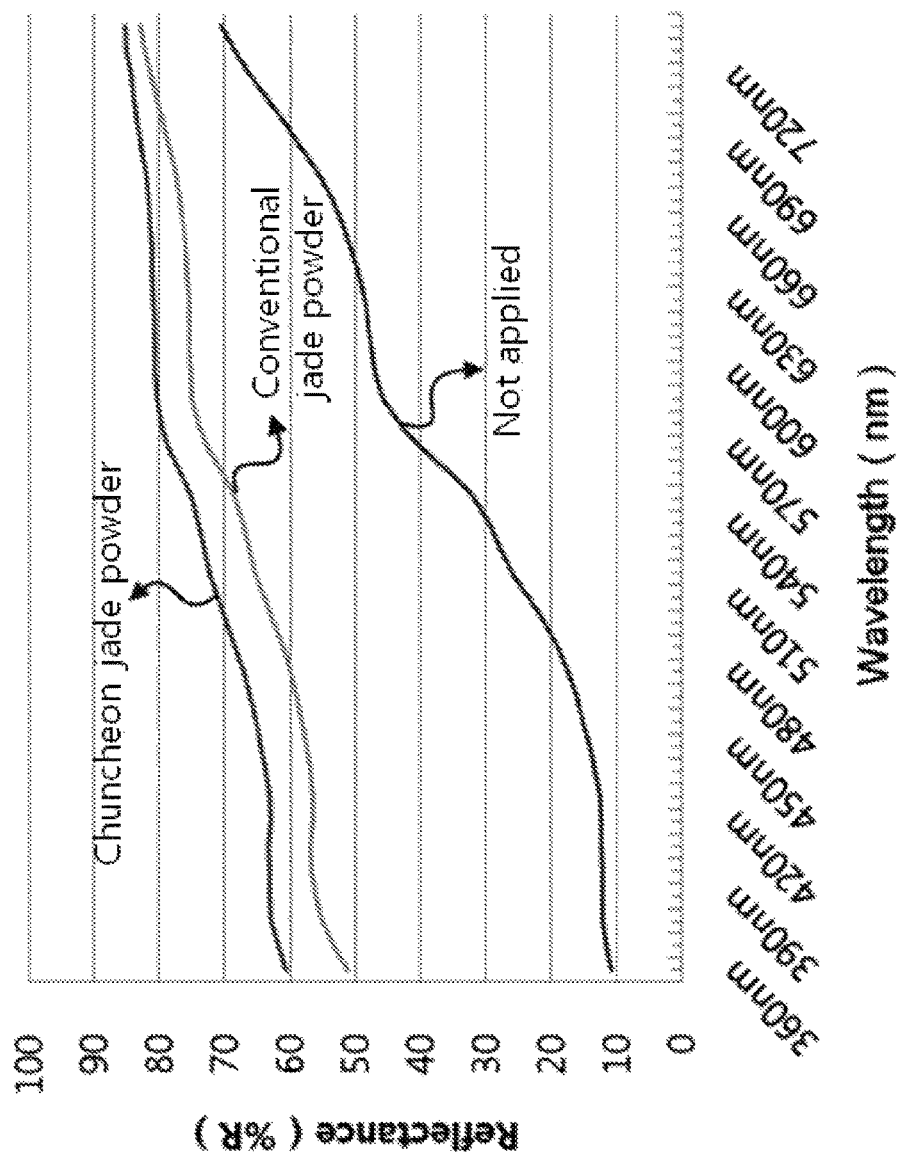
FIG. 2 shows the reflectance spectra of conventional jade powder and Chuncheon jade powder in a wavelength range of 360 to 740 nm when the conventional jade powder and the Chuncheon jade powder are applied onto artificial leather.

FIG. 2 shows the reflectance spectra of the conventional jade powder and the Chuncheon jade powder in a wavelength range of 360 to 740 nm when the conventional jade powder and the Chuncheon jade powder are applied onto artificial leather. As seen from the data of FIG. 2, it was revealed that the artificial leathers coated with the conventional jade powder and the Chuncheon jade powder had higher reflectance over the entire visible light spectrum (380 to 740 nm), compared to the artificial leathers not coated with the conventional jade powder and the Chuncheon jade powder, particularly that there was a significant difference in reflectance as the wavelengths reached the high energy spectrum with short wavelengths. Therefore, the conventional jade powder and the Chuncheon jade powder had specifically high light-blocking rates in the blue light spectrum (380 to 500 nm). In particular, the reflectance of the Chuncheon jade powder in the entire visible light spectrum was measured to be higher over the entire wavelength range, compared to that of the conventional jade powder.

Experimental Example 3. Measurement of Reflectance (% R) in Human Skin

To measure the reflectances (light-blocking rates) of the conventional jade powder and the Chuncheon jade powder at specific wavelengths, the powder of each of the conventional jade powder and the Chuncheon jade powder was applied onto the human skin at a content of 1 mg/cm', and the spectra on the powder-coated human skins at 360 to 740 nm were analyzed using a spectrophotometer.

Figure 3:
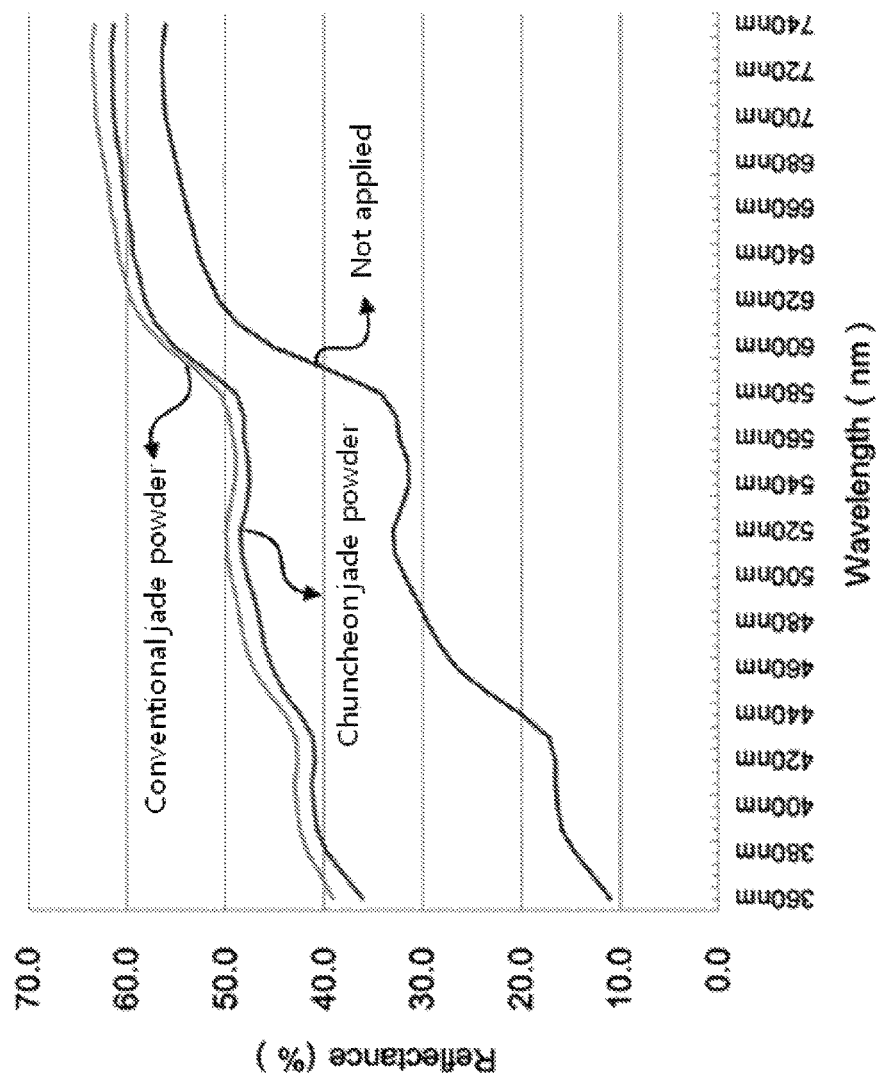
FIG. 3 shows the reflectance spectra of the conventional jade powder and the Chuncheon jade powder in a wavelength range of 360 to 740 nm when the conventional jade powder and the Chuncheon jade powder are applied onto human skins.

FIG. 3 shows the reflectance spectra of the conventional jade powder and the Chuncheon jade powder in a wavelength range of 360 to 740 nm when the conventional jade powder and the Chuncheon jade powder are applied onto human skins. As seen from the data of FIG. 3, it was revealed that the human skins coated with the conventional jade powder and the Chuncheon jade powder had higher reflectance over the entire visible light spectrum (380 to 740 nm), compared to the human skins not coated with the conventional jade powder and the Chuncheon jade powder, particularly that there was a significant difference in reflectance as the wavelengths reached the high energy spectrum with short wavelengths. Therefore, the conventional jade powder and the Chuncheon jade powder had specifically high light-blocking rates in the blue light spectrum (380 to 500 nm). In particular, the reflectance of the conventional jade powder in the entire visible light spectrum was measured to be higher over the entire wavelength range, compared to that of the Chuncheon jade powder, unlike the artificial leathers.

Examples 1 to 3 and Comparative Example 1. Preparation of Jade Powder-Containing Cosmetic Compositions (1) Preparation of Jade Powder-Containing Cosmetic Compositions Cosmetic compositions were formulated to contain 0%, 0.1%, 0.5%, and 1% Chuncheon jade powder, based on the total weight of the cosmetic composition, as listed in the following Table 1.

TABLE 1

| Component names (INCI names) (% by weight) | Comparative Example 1 (0% jade) | Example 1 (0.1% jade) | Example 2 (0.5% jade) | Example 3 (1% jade) |
| --- | --- | --- | --- | --- |
| Cetearyl alcohol | 1.5 | 1.5 | 1.5 | 1.5 |
| Glyceryl stearate SE | 0.5 | 0.5 | 0.5 | 0.5 |
| Polysorbate 60 | 1.2 | 1.2 | 1.2 | 1.2 |
| Sorbitan stearate | 0.3 | 0.3 | 0.3 | 0.3 |
| PEG-40 stearate | 1 | 1 | 1 | 1 |
| Diisostearyl malate | 2 | 2 | 2 | 2 |
| Cetyl ethylhexanoate | 2 | 2 | 2 | 2 |
| *Mangifera indica* (mango) seed butter | 1 | 1 | 1 | 1 |
| Cyclopentasiloxane | 2.5 | 2.5 | 2.5 | 2.5 |
| Cyclohexasiloxane | 1.5 | 1.5 | 1.5 | 1.5 |
| Dimethicone | 2 | 2 | 2 | 2 |
| Disodium EDTA | 0.05 | 0.05 | 0.05 | 0.05 |
| Glycerin | 5 | 5 | 5 | 5 |
| Chuncheon jade powder | 0 | 0.1 | 0.5 | 1 |
| Betaine | 1 | 1 | 1 | 1 |
| Tromethamine | 0.15 | 0.15 | 0.15 | 0.15 |
| Phenoxyethanol | 0.4 | 0.4 | 0.4 | 0.4 |
| Glyceryl caprylate | 0.1 | 0.1 | 0.1 | 0.1 |
| Ethylhexylglycerin | 0.05 | 0.05 | 0.05 | 0.05 |
| Butylene glycol | 8 | 8 | 8 | 8 |
| Hydroxyethyl-acrylate/sodium acryloyldimethyl taurate copolymer | 1 | 1 | 1 | 1 |
| Carbomer | 0.2 | 0.2 | 0.2 | 0.2 |
| Water | 68.55 | 68.45 | 68.05 | 67.55 |
| Total | 100 | 100 | 100 | 100 |

(2) Blue Light-Blocking Effects of Cosmetic Compositions

To check the blue light-blocking effects of the cosmetic compositions prepared as listed in Table 1, an experimental method designed by Scinco Co. Ltd. (#627, Bongeunsa-ro, Gangnam-gu, Seoul, Korea) was carried out using a color spectrophotometer (Model: ColorMate).

Figure 4:
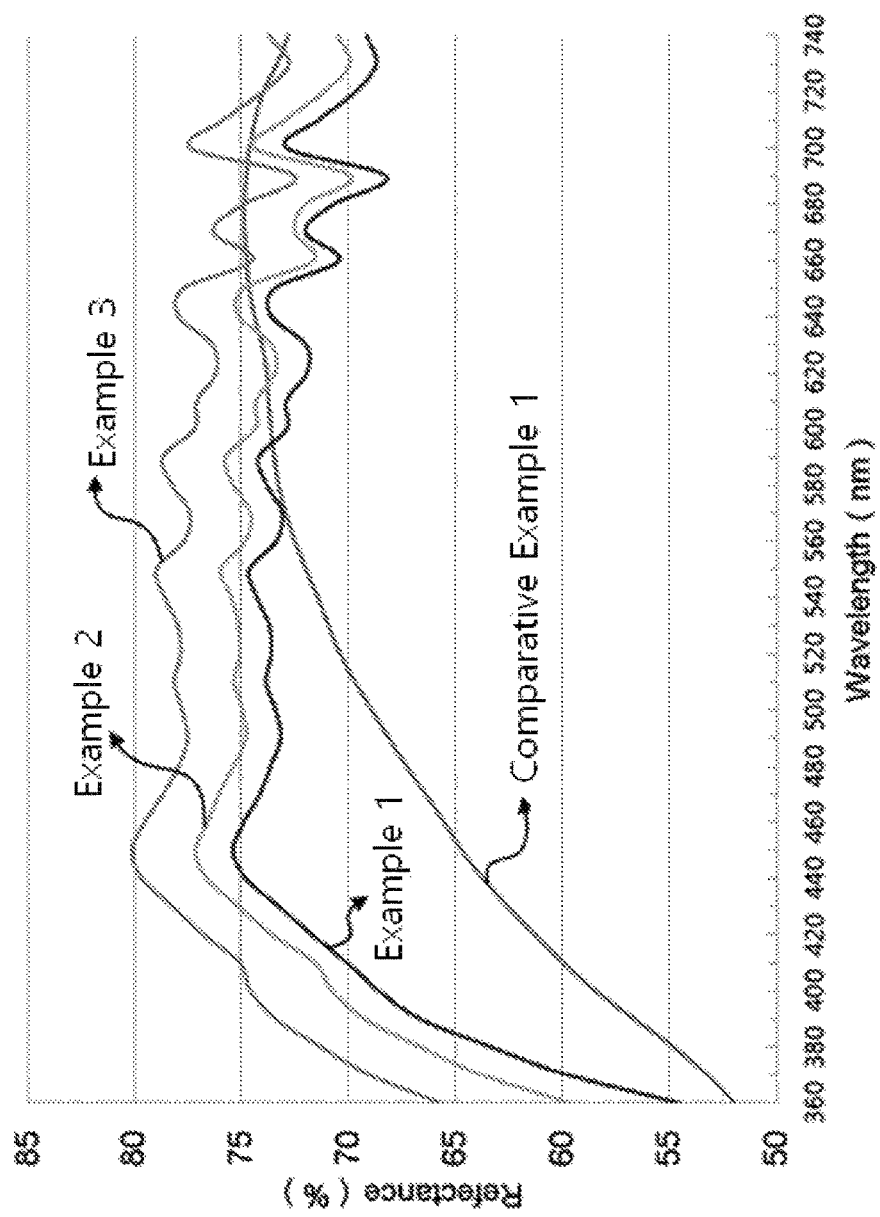
FIG. 4 shows the reflectance spectra of cosmetic compositions of Comparative Example 1 and Examples 1 to 3 in a wavelength range of 360 to 740 nm.

FIG. 4 shows the reflectance spectra of the cosmetic compositions prepared in Comparative Example 1 and Examples 1 to 3 in a wavelength range of 360 to 740 nm. As seen from the data of FIG. 4, it was revealed that the higher reflectance in the blue light spectrum (380 to 500 nm) was stably maintained when the cosmetic compositions of Examples 1 to 3 containing the Chuncheon jade powder were compared to the cosmetic composition of Comparative Example 1 containing no Chuncheon jade powder. Also, it was confirmed that the cosmetic compositions had a higher blue light-blocking effect as the content of the Chuncheon jade powder increased.

INDUSTRIAL APPLICABILITY

The cosmetic composition containing jade powder according to the present invention can be applied as cosmetics having an effect of blocking blue light.

The invention claimed is:

1. A cosmetic composition for blocking blue light, comprising
Chuncheon jade powder as an active ingredient, and
cetearyl alcohol,
glyceryl stearate SE,
polysorbate 60,
sorbitan stearate,
PEG-40 stearate,
diisostearyl malate,
cetyl ethylhexanoate,
*mangifera indica*(mango) seed butter,
cyclopentasiloxane,
cyclohexasiloxane,
dimethicone,
disodium EDTA,
glycerin,
betaine,
tromethamine,
phenoxyethanol,
glyceryl caprylate,
ethylhexylglycerin,
butylene glycol,
hydroxyethylacrylate/sodium acryloyldimethyl taurate copolymer,
carbomer, and
water,
wherein the blue light is visible light having a wavelength of between 380 to 500 nm.

2. The cosmetic composition of claim 1, wherein the jade powder has a particle size of between 10 nm to 100 μm.

3. The cosmetic composition of claim 1, wherein the jade powder is included at a content of between 0.05 to 5.0% by weight, based on the total weight of the cosmetic composition.

4. The cosmetic composition of claim 1, wherein the cosmetic composition is formulated into any one form selected from the group consisting of toners, lotions, creams, sera, emulsions, nourishing serums, powders, foundations, sprays, mask packs, sheet packs, sleeping packs, wash-off packs, and peel-off packs.

* * * * *